United States Patent
Liu et al.

(10) Patent No.: US 11,191,510 B2
(45) Date of Patent: Dec. 7, 2021

(54) IMAGING SYSTEM AND METHOD BASED ON MULTIPLE-GAMMA PHOTON COINCIDENCE EVENT

(71) Applicant: Tsinghua University, Beijing (CN)

(72) Inventors: Yaqiang Liu, Beijing (CN); Tianyu Ma, Beijing (CN); Peng Fan, Beijing (CN)

(73) Assignee: TSINGHUA UNIVERSITY, Beijing (CN)

( * ) Notice: Subject to any disclaimer, the term of this patent is extended or adjusted under 35 U.S.C. 154(b) by 339 days.

(21) Appl. No.: 16/068,699

(22) PCT Filed: May 22, 2017

(86) PCT No.: PCT/CN2017/085404
§ 371 (c)(1),
(2) Date: Jul. 9, 2018

(87) PCT Pub. No.: WO2018/040623
PCT Pub. Date: Mar. 8, 2018

(65) Prior Publication Data
US 2019/0015062 A1 Jan. 17, 2019

(30) Foreign Application Priority Data
Aug. 31, 2016 (CN) .......................... 201610798146.4

(51) Int. Cl.
*A61B 6/00* (2006.01)
*A61B 6/03* (2006.01)
(Continued)

(52) U.S. Cl.
CPC ............ *A61B 6/5282* (2013.01); *A61B 6/037* (2013.01); *A61B 6/06* (2013.01); *A61B 6/4266* (2013.01); *G01T 1/161* (2013.01); *G01T 1/17* (2013.01); *G01T 1/29* (2013.01); *A61B 6/03* (2013.01)

(58) Field of Classification Search
CPC ......... A61B 6/5282; A61B 6/037; A61B 6/06; A61B 6/4266; A61B 6/03; A61B 6/5205;
(Continued)

(56) References Cited

U.S. PATENT DOCUMENTS 5,811,813 A * 9/1998 Maor .................... G01T 1/1642
250/363.04
6,175,116 B1 1/2001 Gagnon et al.
(Continued)

FOREIGN PATENT DOCUMENTS

CN 1203668 12/1998
CN 1481510 3/2004
(Continued)

OTHER PUBLICATIONS

EPO, Office Action for EP Application No. 17844930.2, dated Apr. 1, 2020.
(Continued)

*Primary Examiner* — Christopher Koharski
*Assistant Examiner* — Kaitlyn E Selmer
(74) *Attorney, Agent, or Firm* — Hodgson Russ LLP

(57) ABSTRACT

Provided are an imaging system and method based on multiple-gamma photon coincidence events. The imaging system includes: a plurality of detector assemblies arranged in a non-parallel manner, a time coincidence module and a computer platform. Each detector assembly includes a collimator and a detector configured to measure time and to detect a multiple-gamma photon coincidence event constituted by a plurality of single-gamma photon events cascade-emitted by a radionuclide within a short time. The method is configured to determine validity of the multiple-gamma photon coincidence event, calculate a plurality of non-parallel projection lines where the decay of the radionuclide takes place, determine a location where the decay of the
(Continued)

radionuclide takes place according to the non-parallel projection lines, and obtain a distribution of the radionuclide in the subject according to the location where the decay of the radionuclide takes places.

17 Claims, 3 Drawing Sheets

(51) Int. Cl.
*A61B 6/06* (2006.01)
*G01T 1/161* (2006.01)
*G01T 1/17* (2006.01)
*G01T 1/29* (2006.01)

(58) Field of Classification Search
CPC .... A61B 6/54; G01T 1/29; G01T 1/17; G01T 1/161
See application file for complete search history.

(56) References Cited

U.S. PATENT DOCUMENTS

| | | | |
|---|---|---|---|
| 6,727,502 B1* | 4/2004 | Matthews | G01T 1/1644 250/363.02 |
| 9,395,449 B2* | 7/2016 | Mu | A61B 6/037 |
| 2007/0002307 A1* | 1/2007 | Zaugg | G01C 3/08 356/5.01 |
| 2008/0111081 A1 | 5/2008 | Chuang | |
| 2010/0294941 A1* | 11/2010 | Chuang | G01T 1/2985 250/363.04 |
| 2014/0008542 A1 | 1/2014 | Olcott et al. | |
| 2014/0163368 A1* | 6/2014 | Rousso | G01T 1/1615 600/436 |
| 2016/0131774 A1* | 5/2016 | Lage | A61B 6/5258 600/426 |

FOREIGN PATENT DOCUMENTS

| | | |
|---|---|---|
| CN | 102648856 | 8/2012 |
| CN | 105395208 | 3/2016 |
| CN | 106108934 | 11/2016 |
| WO | 2014012182 | 1/2014 |

OTHER PUBLICATIONS

JPO, Office Action for JP Application No. 2018545651, dated Jul. 16, 2019.
SIPO, Office Action for CN Application No. 201610798146.4, dated Aug. 28, 2018.
WIPO, ISR for Application No. PCT/CN2017/085404, Aug. 8, 2017.

* cited by examiner

IMAGING SYSTEM AND METHOD BASED ON MULTIPLE-GAMMA PHOTON COINCIDENCE EVENT

CROSS-REFERENCE TO RELATED APPLICATION

This application is a U.S. national phase application of International Application No. PCT/CN2017/085404, filed on May 22, 2017, which claims a priority to and benefits of Chinese Patent Application Serial No. 201610798146.4, filed with the State Intellectual Property Office of P. R. China by Tsinghua University on Aug. 31, 2016, the entire content of which is incorporated herein by reference.

FIELD

The present disclosure relates to the field of nuclear medical imaging, and particularly to an imaging system based on cascade gamma photon coincidence event and an imaging method.

BACKGROUND

Nuclear medical imaging, one of the most important technical means for disease diagnosis in modern medicine, is capable of acquiring diagnostic information of diseases by observing metabolism in an organ of organisms non-invasively on a basis of distribution of radiopharmaceutical, obtained by detecting, outside a patient's body, X-rays or gamma photons emitted from radionuclides, which are labeled on molecules involving in physiological metabolism in the organisms, and by image reconstruction. In the field of nuclear medical imaging, the two most important imaging systems are Positron Emission Tomography (PET) and Single-Photon Emission Computed Tomography (SPECT), which are now widely used in clinical examination and diagnosis of diseases, including cancers, neurological diseases and cardiovascular diseases.

Core components of PET consist of several gamma photon detector modules with time measurement functions and corresponding time coincidence modules. The basic principle of PET involves electronic collimation technology and the radionuclides used therein are positron nuclides. The positrons, emitted by the positron nuclides, annihilates in the body of the organisms, generating a pair of gamma photons in almost opposite directions each with an energy of 511 keV. With time coincidence measurement, i.e., if a pair of gamma photons each with an energy of 511 keV are detected by two gamma photon detector modules within a very short period of time (usually within a few nanoseconds) respectively, the two photons are regarded as annihilation photons and it is possible to determine a line of response (LOR) where positron annihilation occurs (approximate to where decay of positron nuclides takes place). With record of a large number of such LORs, a distribution of locations where positron annihilations occur (approximate to the distribution of positron nuclides in the organisms) can be obtained through the image reconstruction. As emission directions of the pair of gamma photons generated by the positron annihilation are almost opposite, it is only possible to determine that the positron annihilation occurs along the corresponding LOR, but impossible to determine a specific location where the positron annihilation takes place at the corresponding LOR. Although it is possible to preliminary determine a position range where the positron annihilation occurs at the corresponding LOR through Time-of-Flight (TOF) measurement technology, the gamma photon detector modules are required to have extremely high time resolution. As the location where the positron annihilation occurs at the corresponding LOR is uncertain, the signal-to-noise ratio (SNR) of the reconstructed image showing the distribution of the positron nuclides in the organisms is often low, which adversely affects the diagnostic effect. In order to improve the image SNR, it is usually required to accumulate a large number of LORs, which needs a patient to intake a relatively high dose of positron nuclides, thereby increasing irradiation risk to the patient.

Core components of SPECT include a collimator, a gamma photon detector module and the like. SPECT involves a physical collimation technique and nuclides used therein are gamma photon nuclides. The collimators are usually arranged in front of the gamma photon detector module to limit the angle at which a gamma photon emitted by the gamma photon nuclides reaches the detector module, such that the gamma photon emitted only along a series of specific directions can pass through the collimator and be detected by the detector module. Every time a gamma photon is detected by the gamma photon detector, it is possible to determine a projection line where the gamma photon is initially emitted. Accordingly, distribution of initial emission locations of gamma photons (i.e., distribution of nuclides emitting gamma photon in the organisms) can be determined by accumulation of a large number of such projection lines and image reconstruction. Similar to PET, SPECT cannot determine a specific location where the gamma photon is emitted at the projection line, and thus the SNR of the reconstructed image is poor. Further, as the collimator is used in SPECT, which limits the angle at which the gamma photon emitted can be detected by the gamma photon detector, resulting in a low detection efficiency, which further deteriorates the SNR of the reconstructed image.

SUMMARY

In embodiments of the present disclosure, there are provided an imaging system and an imaging method based on multiple-gamma photon coincidence events, a device and a non-transitory computer storage medium, aiming at improving detection efficiency of the imaging system and the SNR of a reconstructed image.

In an embodiment of an aspect of the present disclosure, there is provided an imaging system based on multiple-gamma photon coincidence events, including:
a plurality of detector assemblies each including:
a detector, configured to detect a single-gamma photon event and measure time; and
a collimator, arranged in front of the detector such that the single-gamma photon event generated during decay of a radionuclide in a subject to be imaged and emitted only along a set direction is detected by the detector;
a time coincidence module, provided with a time window;
a computer platform;
a timing signaling line, connecting the detector and the time coincidence module; and
an energy and location signaling line, connecting the detector and the computer platform,
wherein the time coincidence module is configured to determine, with the time window, whether a plurality of single-gamma photon events detected by the detectors constitute a multiple-gamma photon coincidence event and input a determination result to the computer platform, wherein the computer platform is configured to determine validity of the multiple-gamma photon coincidence event and determine a location where the decay of the radionuclide takes place according to non-parallel projection lines along which gamma photons are emitted.

Another object of embodiments of the present disclosure is to provide an imaging method of the imaging system mentioned above, the method includes:

(1) starting the imaging system,
injecting radiopharmaceutical labeled with a radionuclide to a subject to be imaged, and
setting an acquisition time for the imaging system, a time window for a time coincidence module, a plurality of energy windows for detectors according to the radionuclide, and a length threshold for determining validity of a multiple-gamma photon coincidence event;

(2) determining, with a computer platform, whether an imaging process is completed according to the acquisition time,
if yes, executing step (5),
if no, executing step (3);

(3) determining, with the time coincidence module, whether a plurality of single-gamma photon evens detected by the detectors are within the time window,
if yes, determining the plurality of single-gamma photon events detected by the detectors constitute the multiple-gamma photon coincidence event and executing step (4),
if no, executing step (2);

(4) determining, with the computer platform, whether energies of the plurality of single-gamma photon evens in the multiple-gamma photon coincidence event each are within a corresponding energy window, according to energy information of the plurality of single-gamma photon events output by the detectors,
if no, discarding the multiple-gamma photon coincidence event,
if yes,
calculating a plurality of non-parallel projection lines where the decay of the radionuclide takes place according to position information of the plurality of single-gamma photon events output by the detectors, and determining via calculating a point to which the sum of individual distances from the plurality of non-parallel projection lines is minimum, and
determining whether a distance from the point to each projection line is lower than or equal to the length threshold,
if yes, recording the point as a location where the decay of the radionuclide takes place,
if no, discarding the multiple-gamma photon coincidence event and executing step (2), (5) obtaining a distribution of the radionuclide in the subject according to the location where the decay of the radionuclide takes place,
wherein gamma photons are cascade-emitted, and the number of the non-parallel projection lines is greater than or equal to 2 but not more than the number of the gamma photons cascade-emitted by the radionuclide in each decay.

Another object of embodiments of the present disclosure is to provide a device, including:
a processor;
a memory; and
a procedure, stored in the memory, and when executed by the processor, causing the processor to perform the imaging method mentioned above.

Another object of embodiments of the present disclosure is to provide a non-transitory computer storage medium having stored therein one or more procedures that, when executed by a device, causes the device to perform imaging method mentioned above.

BRIEF DESCRIPTION OF THE DRAWINGS

These and other aspects and advantages of embodiments of the present disclosure will become apparent and more readily appreciated from the following descriptions made with reference to the drawings, in which.

DETAILED DESCRIPTION

With reference to the drawings and examples, an imaging system and method based on multiple-gamma photon coincidence events will be described in detail as follows.

Figure 1:
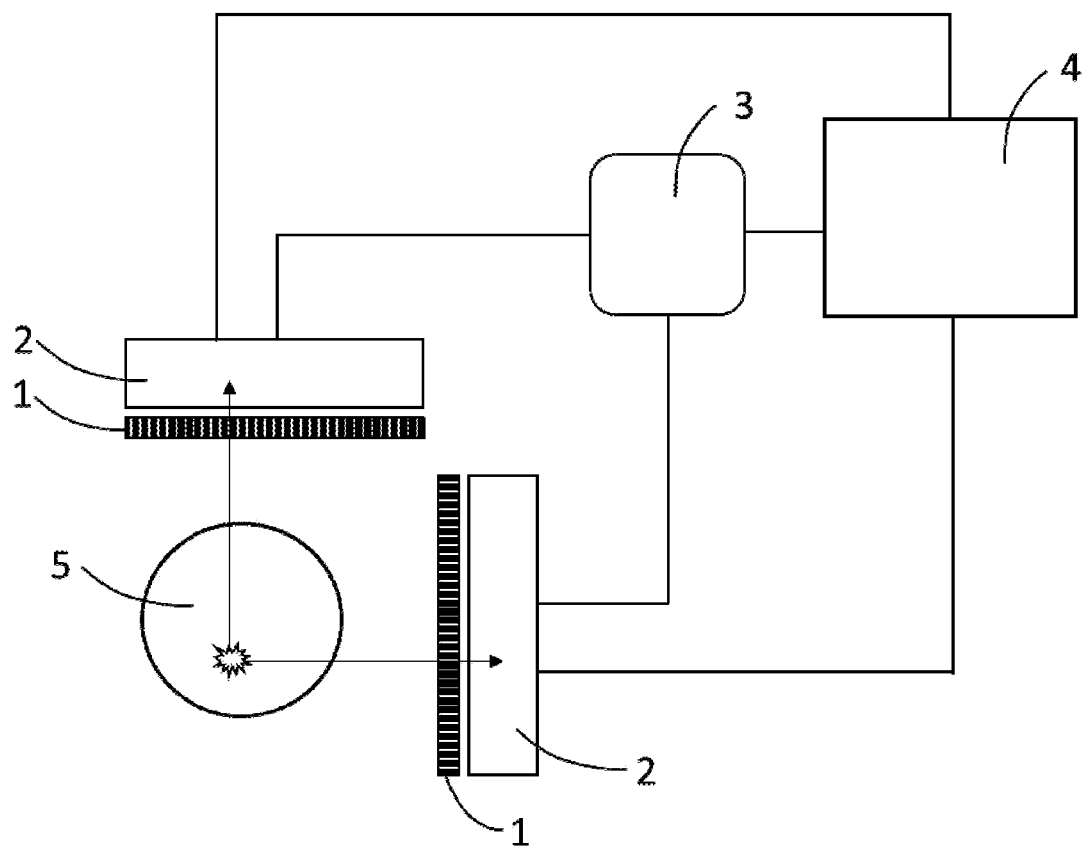
FIG. 1 is a schematic diagram illustrating an imaging system with a parallel-hole collimator, according to an embodiment of the present disclosure.

An overall structure of an imaging system according to an embodiment of the present disclosure is shown in FIG. 1. The imaging system includes two detector assemblies, a time coincidence module 3, a computer platform 4, a timing signaling line and an energy and location signaling line. The two detector assemblies are arranged in such a manner that detecting planes thereof are perpendicular to each other. Each detector assembly includes a detector 2 configured to detect a single-gamma photon event and measure time and a parallel-hole collimator 1 arranged in front of the detector 2 such that the single-gamma photon event generated during decay of a radionuclide in a subject 5 to be imaged and emitted only along a set direction (such as a direction perpendicular to the detecting plane of the detector 2) is detected by the detector 2. The subject 5 to be imaged may be an organism or a standardized imaging phantom of a nuclear medical imaging system. The timing signaling line connects the detector 2 and the time coincidence module 3. The time coincidence module 3 is provided with a time window (which is adjustable according to the radionuclide and generally within hundreds of nanoseconds) and configured to determine, with the time window, whether the single-gamma photon events detected by the two detectors constitute a multiple-gamma photon coincidence event and input a corresponding determination result to the computer platform 4. The energy and location signaling line connects the detector 2 and the computer platform 4. The computer platform 4 is configured to calculate non-parallel projection lines along which gamma photons are emitted so as to determine a location where the decay of the radionuclide takes place.

The parallel-hole collimator 1 used in this example includes a rectangular tungsten alloy plate where the tungsten alloy has a strong absorption to the gamma photon. Several parallel collimating holes are arranged at an equal interval on the rectangular plate such that gamma photons emitted only along the hole can pass through the collimator and be detected by the detector 2. In this example, the collimator is of a thickness of 4 mm, each collimating hole is of a diameter of 2 mm and a wall thickness of 2 mm.

The detector 2 used in this example is a NaI(Tl) scintillator detector which uses a continuous NaI(Tl) crystal, is of a size of 585 mm (length)×470 mm (width)×9.5 mm (thickness), and is coupled to 55 photomultipliers (PMTs) at an end of the NaI(Tl) crystal opposite to the collimator for photoelectric signal conversion so as to achieve measurement of the position, energy and time information of the gamma photon in the crystal.

In addition to indium 111, a radiopharmaceutical used in the imaging system according to the present disclosure may also be labeled with other radionuclides which are capable of generating at least two gamma photons in a cascade manner within a short time during each decay, including but not limited to sodium 22, iodine 131, thallium 201, rubidium 82, yttrium 90, and the like.

Figure 2:
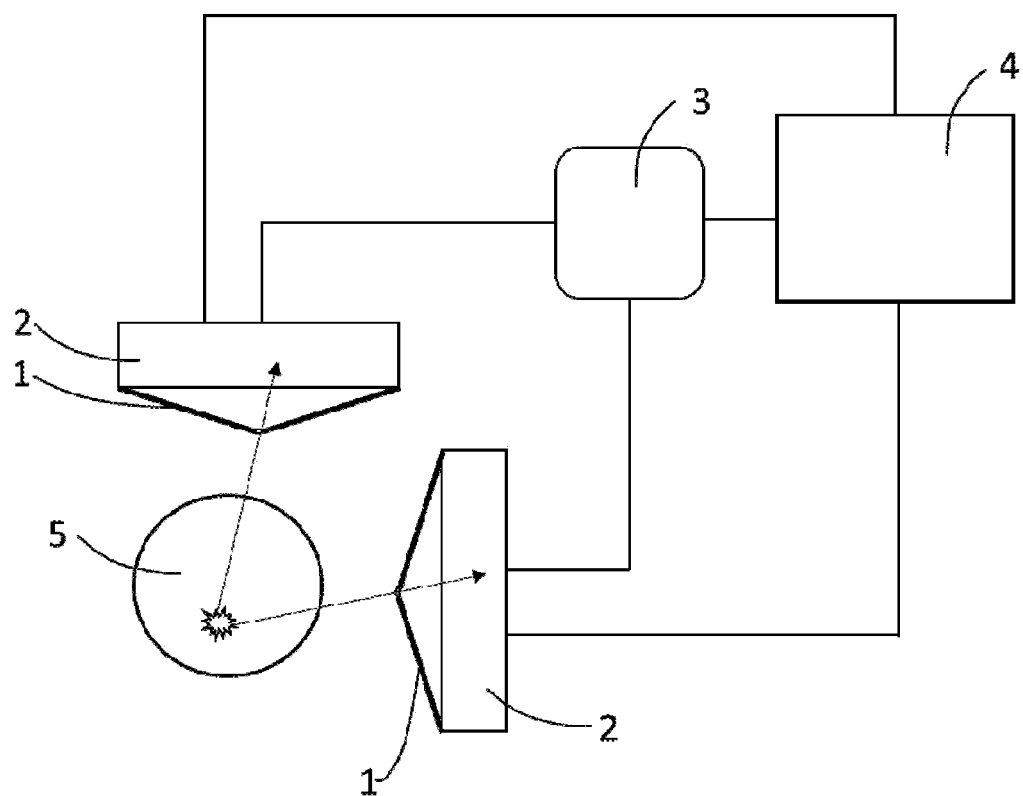
FIG. 2 is a schematic diagram illustrating an imaging system with a pinhole collimator, according to an embodiment of the present disclosure.

In addition to the parallel-hole collimator as shown in FIG. 1, the collimator used in the imaging system according to the present disclosure may also be a pinhole collimator (as shown in FIG. 2), a convergent collimator or a divergent collimator and the like, all of which are conventional products. In embodiments of the present disclosure, the type and parameters of the collimator can be selected according to factors such as field of view (FOV), spatial resolution and detection efficiency of the imaging system to be achieved.

In addition to two detector assemblies used in the imaging system in this example, in other examples, the imaging system may include more than two detector assemblies, the more than two detector assemblies are arranged in such a manner that at least two detecting planes thereof are non-parallel one another, such as in circular, square or polygonal manner. The number and arrangement manners of the detector assemblies may be selected according to the detection efficiency of the imaging system to be achieved. The detection efficiency of the imaging system is higher with the number of probes increases.

The imaging system according to embodiments of the present disclosure positions where the decay of the radionuclide takes place by determining via calculation a point to which the sum of individual distances from two or more non-parallel projection lines is minimum, and acquires the distribution of the radionuclide in the organism, which effectively overcomes shortcomings of the conventional PET or SPECT system that it is only possible to determine an LOR or a projection line along which the decay of the radionuclide takes place, but impossible to determine a specific location where the decay of the radionuclide takes place at the LOR or the projection line. As the location where the decay of the radionuclide takes place can be determined via calculation based on several non-parallel projection lines, the image reconstruction algorithm is simplified and the SNR of the reconstructed image is improved. At the same time, there is no need to accumulate a large number of projection lines to reconstruct a spatial distribution of radionuclides, thereby reducing the total demand for gamma photon events, the intake amount of radiopharmaceutical by the patient, and the radiation risk to the patient to a certain extent.

Figure 3:
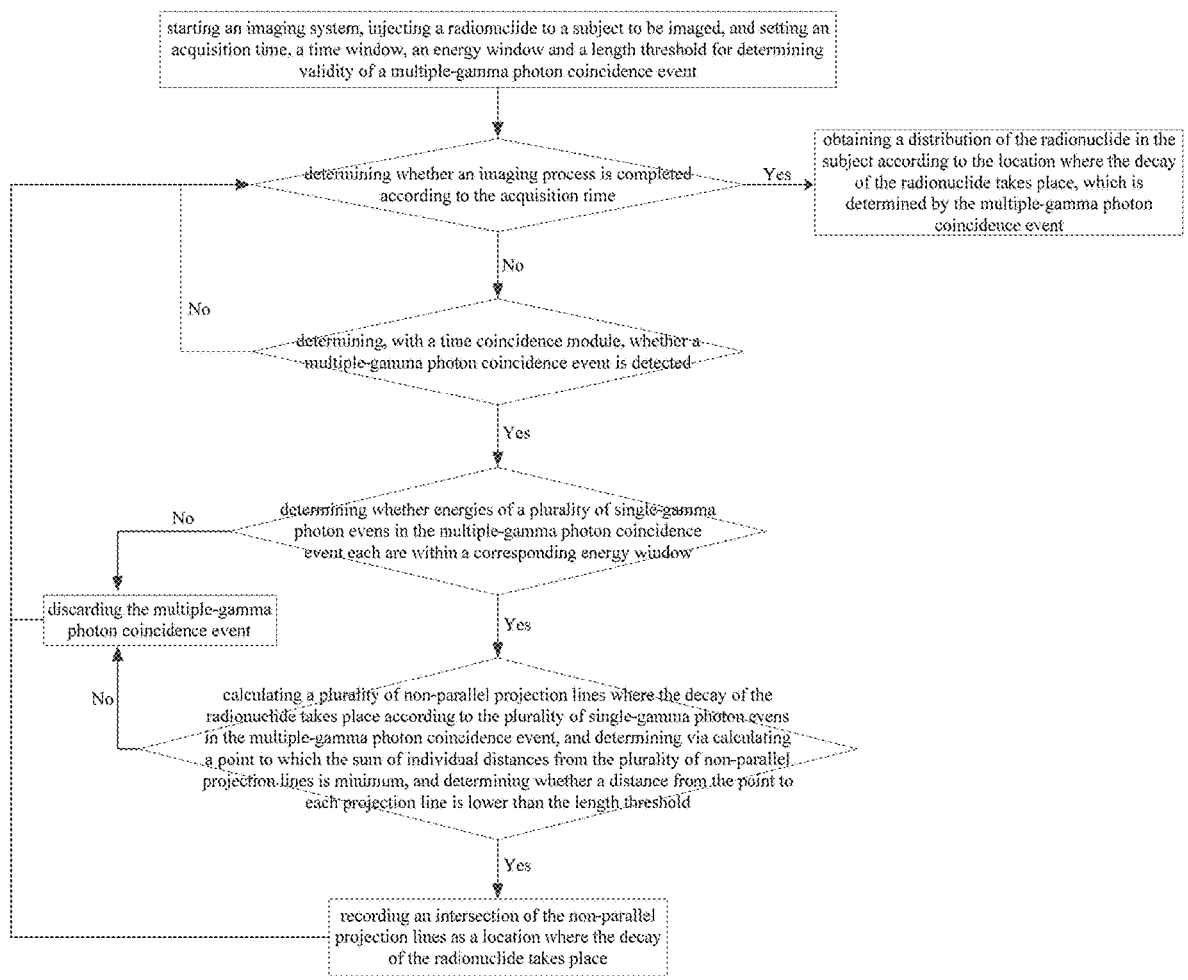
FIG. 3 is a flow chart illustrating an imaging method of the imaging system shown in FIG. 1 or FIG. 2.

A flow chart of an imaging method of the imaging system according to an embodiment of the present disclosure is shown in FIG. 3. Referring to FIG. 3, an implementation of the imaging method includes:

(1) starting the imaging system;
setting an acquisition time to be 20 min, a time window for a time coincidence module 3 to be 200 ns, which is adjustable according to the type of radionuclide used; a length threshold to be 5 mm for determining validity of a multiple-gamma photon coincidence event, which is adjustable according to a type and parameter of a collimator used in the imaging system and spatial resolutions of detectors 2, a plurality of energy windows for the detectors 2 according to a radionuclide used;

injecting a radiopharmaceutical labeled by indium 111 with an activity of 4 mCi to a subject 5 to be imaged, where the indium 111 as the radionuclide used in the example is capable of generating two gamma photons (their energies are 171 keV and 245 keV, respectively) in a cascade manner in a short time (which depends on the type of radionuclide, typically within hundreds of nanoseconds) in each decay; on this basis, the energy windows are set for each detector 2 to be 171 keV±10% and 245 keV±10%, respectively, it should be appreciated that, the number of energy windows for each detector 2 is adjustable according to the number of gamma photons emitted in the cascade manner by the used radionuclide, i.e., gamma photons with different energies each corresponds to one energy window, and the range of each energy window is adjustable according to the energy resolution of the detector 2;

(2) determining, with a computer platform 4, whether an imaging process is completed according to the acquisition time,
if yes, executing step (5),
if no, executing step (3);

(3) determining, with the time coincidence module 3, whether a multiple-gamma photon coincidence event is detected by the detector 2,
if yes, executing step (4),
if no, executing step (2);

it should be illustrated that term "multiple-gamma photon coincidence event" used in the present disclosure means that if two or more single-gamma photon events detected by the detectors are within the time window of the time coincidence module 3, the two or more single-gamma photon events constitute the multiple-gamma photon coincidence event;

(4) determining, with the computer platform 4, whether energies of two single-gamma photon events in the multiple-gamma photon coincidence event each are within the corresponding energy window, according to energy information of the two single-gamma photon events output by the detectors 2,
if no, discarding the multiple-gamma photon coincidence event,
if yes,
calculating two non-parallel projection lines where the decay of the radionuclide takes place according to position information of the two single-gamma photon events output by the detectors 2, and determining via calculating a point to which the sum of individual distances from the two non-parallel projection lines is minimum, and determining whether a distance from the point to each projection line is lower than or equal to the length threshold,
if yes, recording the point as a location where the decay of the radionuclide takes place,
if no, discarding the multiple-gamma photon coincidence event and executing step (2);

(5) obtaining a distribution of the radionuclide in the subject according to the location where the decay of the radionuclide takes place.

It should be appreciated that, the number of the non-parallel projection lines may be at least 2 but not more than the number of the gamma photons cascade-emitted by the radionuclide in each decay, and each single-gamma photon event can determine a projection line where the decay of the radionuclide takes place.

With the imaging system according to embodiments of the present disclosure, the location where the decay of the radionuclide takes place can be determined via a direct calculation, thus, the image reconstruction algorithm is simplified and the SNR of the reconstructed image is improved. At the same time, there is no need to accumulate a large number of projection lines to reconstruct a spatial distribution of radionuclides, thereby reducing the total demand for gamma photon events, the intake amount of radionuclide by the patient, and the irradiation risk to the patient to a certain extent.

The imaging method according to embodiments of the present disclosure can be programmed (which can be realized by a programmer through conventional programming techniques) and input to the computer platform 4. A desired effect can be achieved when the imaging method is executed in accordance with the steps.

In embodiments of the present disclosure, there is further provided a device, including:
- a processor;
- a memory; and
- a procedure, stored in the memory, and when executed by the processor, causing the processor to perform the imaging method mentioned above.

In embodiments of the present disclosure, there is further provided a non-transitory computer storage medium having stored therein one or more procedures that, when executed by a device, causes the device to perform imaging method mentioned above.

Furthermore, a method and system for batch production of multi-layer microfluidic chips, other configurations and functions of the non-transitory computer storage medium are known to those skilled in the art, and will not be elaborated herein.

Reference throughout this specification to "an embodiment," "some embodiments," "one embodiment", "another example," "an example," "a specific example," or "some examples," means that a particular feature, structure, material, or characteristic described in connection with the embodiment or example is included in at least one embodiment or example of the present disclosure. Thus, the appearances of the phrases such as "in some embodiments," "in one embodiment", "in an embodiment", "in another example," "in an example," "in a specific example," or "in some examples," in various places throughout this specification are not necessarily referring to the same embodiment or example of the present disclosure. Furthermore, the particular features, structures, materials, or characteristics may be combined in any suitable manner in one or more embodiments or examples.

Although explanatory embodiments have been shown and described, it would be appreciated by those skilled in the art that the above embodiments cannot be construed to limit the present disclosure, and changes, alternatives, and modifications can be made in the embodiments without departing from spirit, principles and scope of the present disclosure.

What is claimed is:

1. An imaging system based on multiple-gamma photon coincidence events, comprising:
   a plurality of detector assemblies each comprising:
      a detector, configured to detect a single-gamma photon event and measure time; and
      a collimator, arranged in front of the detector such that the single-gamma photon event generated during decay of a radionuclide in a subject to be imaged and emitted only along a set direction is detected by the detector;
   a time coincidence software module, provided with a time window;
   a computer platform;
   a timing signaling line, connecting the detector and the time coincidence software module; and
   an energy and location signaling line, connecting the detector and the computer platform,
   wherein the time coincidence software module is configured to determine, with the time window, whether a plurality of single-gamma photon events detected by the detectors constitute a multiple-gamma photon coincidence event, to determine whether the multiple-gamma photon coincidence event has time coincidence, and input a determination result to the computer platform,
   wherein the computer platform is configured to determine validity of the multiple-gamma photon coincidence event and determine a location where the decay of the radionuclide takes place according to non-parallel projection lines along which gamma photons are emitted,
   wherein the computer platform is further configured to:
      determine whether energies of the plurality of single-gamma photon events in the multiple-gamma photon coincidence event each are within a corresponding preset energy window, according to energy information of the plurality of single-gamma photon events, to determine whether the multiple-gamma photon coincidence event has energy coincidence, if no, discard the multiple-gamma photon coincidence event, if yes, calculate a plurality of non-parallel projection lines where the decay of the radionuclide takes place according to position information of the plurality of single-gamma photon events;
      determine via calculating a point to which the sum of individual distances from the plurality of non-parallel projection lines is minimum;
      determine whether a distance from the point to each projection line is lower than or equal to a preset length threshold, to determine whether the multiple-gamma photon coincidence event has spatial coincidence, if yes, record the point as a location where the decay of the radionuclide takes place, if no, discard the multiple-gamma photon coincidence event, wherein the spatial coincidence comprises determining a correct combination of projection lines from multiple combinations of the projection lines according to a location signaling line and the preset length threshold so as to determine the location where the decay of the radionuclide takes place; and
      obtain a distribution of the radionuclide in the subject according to the location where the decay of the radionuclide takes place;
   wherein the imaging system comprises at least two detector assemblies, the at least two detector assemblies are arranged in such a manner that at least two detecting planes thereof are non-parallel to each other; and
   wherein the preset length threshold is determined according to a parameter of the collimators used in the imaging system and spatial resolutions of the detectors.

2. The imaging system according to claim 1, wherein at least two detecting planes of the at least two detector assemblies are perpendicular to each other.

3. The imaging system according to claim 2, wherein the radionuclide is capable of generating at least two gamma photons in a cascade manner in each decay.

4. An imaging method based on multiple-gamma photon coincidence events, comprising:
(1) starting the imaging system,
injecting radiopharmaceutical labeled with a radionuclide to a subject to be imaged, and
setting an acquisition time for the imaging system, a time window for a time coincidence software module, a plurality of energy windows for detectors according to the radionuclide, and a length threshold for determining validity of a multiple-gamma photon coincidence event;
(2) determining, with a computer platform, whether an imaging process is completed according to the acquisition time,
if yes, executing step (5),
if no, executing step (3);
(3) determining, with the time coincidence software module, whether a plurality of single-gamma photon events detected by the detectors are within the time window, to determine whether the multiple-gamma photon coincidence event has time coincidence,
if yes, determining the plurality of single-gamma photon events detected by the detectors constitute the multiple-gamma photon coincidence event and executing step (4),
if no, executing step (2);
(4) determining, with the computer platform, whether energies of the plurality of single-gamma photon events in the multiple-gamma photon coincidence event each are within a corresponding energy window, according to energy information of the plurality of single-gamma photon events output by the detectors, to determine whether the multiple-gamma photon coincidence event has energy coincidence,
if no, discarding the multiple-gamma photon coincidence event,
if yes,
calculating a plurality of non-parallel projection lines where the decay of the radionuclide takes place according to position information of the plurality of single-gamma photon events output by the detectors, and determining via calculating a point to which the sum of individual distances from the plurality of non-parallel projection lines is minimum, and
determining whether a distance from the point to each projection line is lower than or equal to the length threshold, to determine whether the multiple-gamma photon coincidence event has spatial coincidence,
if yes, recording the point as a location where the decay of the radionuclide takes place,
if no, discarding the multiple-gamma photon coincidence event and executing step (2),
wherein the spatial coincidence comprises determining a correct combination of projection lines from multiple combinations of the projection lines according to a location signaling line and the preset length threshold so as to determine the location where the decay of the radionuclide takes place,
(5) obtaining a distribution of the radionuclide in the subject according to the location where the decay of the radionuclide takes place,
wherein gamma photons are cascade-emitted, and the number of the non-parallel projection lines is greater than or equal to 2 but not more than the number of the gamma photons cascade-emitted by the radionuclide in each decay;

wherein the detectors comprise at least two detector assemblies, the at least two detector assemblies are arranged in such a manner that at least two detecting planes thereof are non-parallel to each other; and
wherein the preset length threshold is determined according to a parameter of the collimators used in the imaging system and spatial resolutions of the detectors.

5. A device, comprising:
a processor;
a memory; and
a procedure, stored in the memory, and when executed by the processor, causing the processor to perform an imaging method based on multiple-gamma photon coincidence events, comprising:
(1) starting the imaging system,
injecting radiopharmaceutical labeled with a radionuclide to a subject to be imaged, and
setting an acquisition time for the imaging system, a time window for a time coincidence software module, a plurality of energy windows for detectors according to the radionuclide, and a length threshold for determining validity of a multiple-gamma photon coincidence event;
(2) determining, with a computer platform, whether an imaging process is completed according to the acquisition time,
if yes, executing step (5),
if no, executing step (3);
(3) determining, with the time coincidence software module, whether a plurality of single-gamma photon events detected by the detectors are within the time window, to determine whether the multiple-gamma photon coincidence event has time coincidence,
if yes, determining the plurality of single-gamma photon events detected by the detectors constitute the multiple-gamma photon coincidence event and executing step (4),
if no, executing step (2);
(4) determining, with the computer platform, whether energies of the plurality of single-gamma photon events in the multiple-gamma photon coincidence event each are within a corresponding energy window, according to energy information of the plurality of single-gamma photon events output by the detectors, to determine whether the multiple-gamma photon coincidence event has energy coincidence,
if no, discarding the multiple-gamma photon coincidence event,
if yes,
calculating a plurality of non-parallel projection lines where the decay of the radionuclide takes place according to position information of the plurality of single-gamma photon events output by the detectors, and determining via calculating a point to which the sum of individual distances from the plurality of non-parallel projection lines is minimum, and
determining whether a distance from the point to each projection line is lower than or equal to the length threshold, to determine whether the multiple-gamma photon coincidence event has spatial coincidence,
if yes, recording the point as a location where the decay of the radionuclide takes place,
if no, discarding the multiple-gamma photon coincidence event and executing step (2),
wherein the spatial coincidence comprises determining a correct combination of projection lines from multiple combinations of the projection lines according to a location signaling line and the preset length threshold so as to determine the location where the decay of the radionuclide takes place, (5) obtaining a distribution of the radionuclide in the subject according to the location where the decay of the radionuclide takes place, wherein gamma photons are cascade-emitted, and the number of the non-parallel projection lines is greater than or equal to 2 but not more than the number of the gamma photons cascade-emitted by the radionuclide in each decay;

wherein the detectors comprise at least two detector assemblies, the at least two detector assemblies are arranged in such a manner that at least two detecting planes thereof are non-parallel to each other; and wherein the preset length threshold is determined according to a parameter of the collimators used in the imaging system and spatial resolutions of the detectors.

6. The imaging system according to claim 1, wherein the time coincidence software module is further configured to determine whether the plurality of single-gamma photon events detected by the detectors are within the time window, if yes, determine that the plurality of single-gamma photon events detected by the detectors constitute the multiple-gamma photon coincidence event.

7. The imaging system according to claim 1, wherein the collimator comprises a pinhole collimator, a convergent collimator or a divergent collimator.

8. The imaging system according to claim 1, wherein the time window is determined according to the radionuclide.

9. The imaging system according to claim 8, wherein the time window is within hundreds of nanoseconds.

10. The imaging system according to claim 2, wherein the more than two detector assemblies are arranged in circular, square or polygonal manner.

11. The imaging system according to claim 3, wherein the radionuclide comprises indium 111, sodium 22, iodine 131, thallium 201, rubidium 82 or yttrium 90.

12. The imaging system according to claim 11, wherein the radionuclide is indium 111.

13. The imaging method according to claim 4, wherein the time window is determined according to the radionuclide.

14. The imaging method according to claim 13, wherein the time window is within hundreds of nanoseconds.

15. The imaging method according to claim 4, wherein the radionuclide is capable of generating at least two gamma photons in a cascade manner in each decay.

16. The imaging method according to claim 15, wherein the radionuclide comprises indium 111, sodium 22, iodine 131, thallium 201, rubidium 82 or yttrium 90.

17. The imaging method according to claim 16, wherein the radionuclide is indium 111.

* * * * *